United States Patent
Weidle et al.

(10) Patent No.: US 6,538,110 B1
(45) Date of Patent: Mar. 25, 2003

(54) MONOCLONAL ANTIBODIES AGAINST THE INTERLEUKIN 2 RECEPTOR

(75) Inventors: Ulrich Weidle, München (DE); Eberhard Russmann, Penzberg (DE); Klaus-Peter Hirth, München (DE); Tiberiu Diamantstein, Berlin (DE); Brigitte Kaluza, Bad Heilbrunn (DE)

(73) Assignee: Roche Diagnostics, Mannheim (DE)

( * ) Notice: Subject to any disclaimer, the term of this patent is extended or adjusted under 35 U.S.C. 154(b) by 0 days.

(21) Appl. No.: 07/988,945

(22) PCT Filed: Sep. 12, 1991

(86) PCT No.: PCT/EP91/01737

§ 371 (c)(1), (2), (4) Date: Mar. 10, 1993

(87) PCT Pub. No.: WO92/04051

PCT Pub. Date: Mar. 19, 1992

(30) Foreign Application Priority Data

Sep. 12, 1990 (DE) ............................................. 40 28 955

(51) Int. Cl.⁷ ..................... C07K 16/28; C07K 14/715; G01N 33/53
(52) U.S. Cl. ............................. 530/388.22; 530/388.1; 530/387.1; 530/387.3; 530/388.73; 530/388.75; 530/388.85; 435/7.1; 435/7.24; 435/7.2
(58) Field of Search ............................. 435/240.27, 7.1, 435/7.24, 7.2; 424/85.8, 143.1, 136.1; 530/387.3, 388.22, 391.1, 388.1, 387.1, 388.73, 388.75, 388.85

(56) References Cited

FOREIGN PATENT DOCUMENTS

WO    WO8909622    10/1989

OTHER PUBLICATIONS

Soulillou, J.P. et al. Monoclonal anti–IL2–receptor in organ transplantation. Transplant Int., 2: 46–52, 1989.*
Taki, S. et al. Biotinylation of human interleukin–2 for flow cytometry analysis of interleukin–2 receptors. J. of Immunological Methods, 122: 33–41, 1989.*
Callat–Zucman, S. et al. In vitro and in vivo action of cyclsporin A and the induction of human interleukin–2 alpha and beta chains. Clin. Exp. Immunol., 77: 184–190, 1989.*
Niguma Transplantation Proceedings 23(1):290, 1991.*
Jacque Et Al. Transplantation Proceeding 23(1):1068, 1991.*
Takashita Et Al. J. Exp. Med. 1989, 169:1323.*
Morrison Et Al. Clin. Chem. vol. 34 No. 4, 1988 1668.*
Queen Et Al. PNAS. 86: 10029, 1989.*
Williams TibTech Feb. 1988, vol. 6, p. 36.*
Hird Genes and Cancer John Wiley & Sons LTD, 1990 183.*
Waldmann Science vol. 252:1657, 1991.*
Harris Et. Al. TibTech 1993 vol. 11 p. 42.*
Kupiec Weglinski Et Al. Eur. J. Immun. 1987; 17:313.*
Weidle Et Al. Journal of Cellular Immunol. Abstract, 1991.*
Kamio et al., *International Immunology*, vol. 2, No. 6, Jun. 1990.

* cited by examiner

Primary Examiner—Anthony C. Caputa
Assistant Examiner—Anne L. Holleran
(74) Attorney, Agent, or Firm—Fulbright & Jaworski, LLP

(57) ABSTRACT

The invention concerns an antibody composition which inhibits the binding of interleukin 2 to its high affinity receptor and contains (1) monoclonal antibodies against the α chain of the interleukin 2 receptor and
(2) monoclonal antibodies against the β chain of the interleukin 2 receptor,
   as well as a pharmaceutical agent which contains the antibody composition according to the present invention.

8 Claims, No Drawings

MONOCLONAL ANTIBODIES AGAINST THE INTERLEUKIN 2 RECEPTOR

When the immune system responds to an antigen various cells of the immune system are activated. These activated cells synthesize a series of lymphokines which then in turn regulate the activation, proliferation and differentiation of further cells of the immune system. The T lymphocytes play a central role in this process the growth of which is controlled by a specific factor, interleukin 2 (IL-2). IL-2 is a lymphokine of 133 amino acids and exerts its growth-promoting properties via binding to specific receptors on the cell surface.

The interleukin 2 receptor (IL-2R) is present in three forms which differ in their composition and in their affinity to the ligand. The low-affinity IL-2R ($K_d=10^{-8}$ M), which is also denoted α chain, light (L) chain, p55 molecule and in humans is also designated CD25 or Tac antigen, is a glycoprotein of 55 kDa molecular weight. The genes for the α chain of the murine, bovine and human IL-2R have been cloned and the amino acid sequences of their protein products have been determined (Miller et al., J. Immunol. 134 (1985) 4212–4217; Nikaido et al., Nature 311 (1984) 631; Weinberg et al., Immunology 63 (1988), 603).

The medium affinity IL-2R ($K_d=10^{-9}$ M), which is also denoted β chain, heavy (H) chain or p75 molecule, is a glycoprotein with a molecular weight of 70 to 75 kDa in the mouse and humans (Tsudo et al., Proc. Natl. Acad. Sci. USA 83 (1986), 9694; Sharon et al., J. Exp. Med. 167 (1988), 1265).

The high affinity IL-2R ($K_d=10^{-11}$ M) is a heterodimer which is composed of non-covalently bound α and β chains (Wang and Smith, J. Exp. Med. 166 (1987), 1156; Waldman, J. Nat. Cancer Institute 81 (1989) 915).

Monoclonal antibodies against the α chain as well as against the β chain of the human IL-2 receptor have been isolated and they have been demonstrated to have an immunosuppressive action in vitro as well as in vivo (Sakagami et al., Transplantation Proceedings Vol. XIX. (1) (1987), 586–590; Kupiec-Weglinski et al., Proc. Natl. Acad. Sci. USA 83 (1986), 2624–2627; Mouzaki et al., Eur. J. Immunol. 17 (1987), 335–341; Olive et al., Eur. J. Immunol. 16 (1986), 611–616; Friend et al., Transplantation Proceedings, Vol. XIX (1987), 4317–4418; Soulillou et al., Lancet, Jun. 13, (1987), 1339–1342; Kupiec-Weglinski et al., Eur. J. Immunol. 17 (1987), 313–319).

Monoclonal antibodies against IL-2R have a high potential for immunosuppressive therapy, in particular for treating graft rejections, adult T cell leukemia and autoimmune diseases such as e.g. rheumatoid arthritis.

It has, however, been shown that the in vivo administration of monoclonal antibodies of animal origin in humans is limited since they are recognized as being foreign and this leads to an immune reaction against the administered antibodies. This immune reaction can be reduced by using so-called chimeric or humanized antibodies. Chimeric antibodies are antibodies in which the constant domains of animal origin (e.g. the mouse) have been replaced by a human constant domain. Humanized antibodies are human antibodies of which only the antigen binding sites of the variable region (the CDR or hypervariable regions) are of animal origin (Verhoeyen and Riechmann, BioEssays 8 (1988), 74–78).

However, even when administering chimerized or humanized antibodies an undesired immune reaction of the patient can be observed in some cases at higher doses, which is caused by the production of anti-idiotypic antibodies.

The object of the present invention is therefore to provide antibodies which are effective in an immunosuppressive therapy and which can be used in substantially lower doses than previously known antibodies.

The present invention concerns an antibody composition which inhibits the binding of interleukin 2 to its high affinity receptor and contains (1) monoclonal antibodies against the α chain of the interleukin 2 receptor and (2) monoclonal antibodies against the β chain of the interleukin 2 receptor.

Surprisingly the combined use of monoclonal antibodies against the α chain as well as against the β chain of the IL-2 receptor in vitro leads to synergistic effects and thus the antibody composition according to the present invention results in a stronger inhibition of the IL-2 induced proliferation of human peripheral blood lymphocytes than when one of the two antibodies is used alone at the corresponding concentration.

An antibody composition according to the present invention preferably contains (1) 1 to 99% in relation to the total antibody amount of monoclonal antibodies against the α chain of the interleukin 2 receptor and (2) 99 to 1% in relation to the total antibody amount of monoclonal antibodies against the β chain of the interleukin 2 receptor.

The composition preferably contains 4 to 96% in relation to the total antibody amount monoclonal antibodies against the α chain of the interleukin 2 receptor and 96 to 4% in relation to the total antibody amount of monoclonal antibodies against the β chain of the interleukin 2 receptor. When the antibody ratio is 4:96 or 96:4, one already finds a five-fold reduction in the total amount of antibody compared to the use of only one monoclonal antibody against the α or the β chain.

The composition according to the present invention is particularly preferred when it contains aproximately equal amounts (1) of monoclonal antibodies against the α chain of the interleukin 2 receptor and (2) monoclonal antibodies against the β chain of the interleukin 2 receptor. At an equimolar ratio of antibodies it is found that the total concentration of monoclonal antibodies required for a 60 to 70% inhibition of the IL-2 action is reduced fifteen-fold.

The composition according to the present invention preferably contains an antibody against the α chain which by itself already causes an inhibition of the interleukin 2 binding. It is also preferred that the composition according to the present invention contains an antibody against the β chain which by itself already causes an inhibition of the interleukin 2 binding. A composition according to the present invention is particularly preferred when it contains in each case an antibody against the α chain and an antibody against the β chain each of which alone already causes an inhibition of the interleukin 2 binding.

The antibody 3G10/179 (ECACC 90071905) which was deposited at the European Collection of Animal Cell Cultures, PHLS Centre for Applied Microbiology & Research Portion Down, Salisbury, U.K. on Jul. 19, 1990, is preferably used as the antibody against the α chain which is present in the composition according to the present invention. However, other antibodies against the α chain of interleukin 2 are also suitable in particular when they by themselves already cause an inhibition of the interleukin 2 binding. The antibodies C68/41 (ECACC 90090704) which was deposited at the European Collection of Animal Cell Cultures, PHLS Centre for Applied Microbiology &

Research Portion Down, Salisbury, U.K. on Sep. 7, 1990, and A23A41 (DSM ACC2015) β which was deposited at DSM-Deutsche Sammlung von Mikroorganismen Und Zellkulturen GmbH, Mascheroder Weg 1B, D-3300 Braunschweig on Jul. 30, 1991, are particularly suitable as the antibody against the β chain of the interleukin 2 receptor as are, antibodies known from the literature such as the Mik/β$_1$ antibody (Tsudo et al., Proc. Natl. Acad. Sci. USA 86 (1989), 1982–1986; Takeshita et al., J. Exp. Med. 169 (1989), 1323–1332).

The composition according to the present invention can also contain a covalent coupling product of a monoclonal antibody against the α chain and a monoclonal antibody against the β chain of the interleukin 2 receptor.

The composition according to the present invention preferably contains one or several chimerized antibodies with human constant domains or humanized antibodies in which the non-hypervariable parts of the variable domain are also replaced by the corresponding human regions. In this case one preferably uses chimerized antibodies whose variable domains have been isolated by new methods described in DE 40 33 120 and in a further corresponding application.

The present invention also encompasses a pharmaceutical agent which contains an antibody composition according to the present invention as well as, if desired, the usual pharmaceutical carrier substances, fillers, auxiliary agents and additives and a process for the production of such a pharmaceutical agent in particular for the immunosuppressive therapy of lymphoproliferative diseases, autoimmune diseases, graft rejections or other disorders in the organism in which T cell proliferation has to be at least temporarily suppressed. The invention furthermore encompasses the use of such a pharmaceutical agent for immunosuppressive therapy.

Finally the invention also encompasses a method for treating disorders of the immune system, in particular for immunosuppression, in which a pharmaceutical agent according to the present invention is administered.

The cell lines which produce the aforementioned antibodies were deposited at the European Collection of Animal Cell Cultures (ECACC), Porton Down (GB) or the "Deutsche Sammlung von Mikroorganismen und Zellkulturen GmbH (DSM), Mascheroder Weg 1b, D-3300 Braunschweig" and assigned the depository numbers:

3G10/179: ECACC 90071905 (Date of deposit: 19.07.1990)

C68/41: ECACC 90090704 (Date of deposit: 07.09.1990)

A23A41: DSM ACC2015 (Date of deposit: 30.07.1991)

The sequences of the variable regions of the antibody A23A41 are described in the attached sequence protocols. Suitable constant regions (murine or human) for this antibody are described in: Sequences of proteins of immunological interest; E. Kabat, T. Wu, M. Reid-Miller, H. Perry and K. Gottesman, US Department of Health and Human Services, 1987, p. 282–325.

It is intended to also elucidate the present invention by the following example in conjunction with the sequence protocols.

SEQ ID NO.1 shows the nucleotide sequence and amino acid sequence of the variable region of the light chain of the anti-IL2Rβ antibody A23A41.

SEQ ID NO. 2 shows the nucleotide sequence and amino acid sequence of the variable region of the heavy chain of the anti-IL2Rβ antibody A23A41.

EXAMPLE 1

1. Pre-activation of human peripheral blood lymphocytes

Peripheral blood lymphocytes are isolated by means of a Ficoll gradient, washed in cell culture medium and incubated with 5 µg/ml concanavalin A at a cell density of 8×10$^5$ cells/ml for 3 days (37° C., 5% $CO_2$). Afterwards the cells are washed with culture medium containing 5 mg/ml methyl-α-mannopyranoside to remove the ConA and are used in the test.

2. Test Procedure

The pre-activated, washed, human peripheral blood lymphocytes are adjusted to 4×10$^6$ cells/ml in culture medium and in each case 25 µl of the cell suspension is incubated for half an hour at room temperature with 25 µl of the monoclonal antibody against the IL-2 receptor (concentration see Table 1) in a 96-well microtitre plate. Afterwards, 25 µl of an IL-2 solution (100 U/ml) is added and the culture is incubated for 48 hours (37° C., 5% $CO_2$).

Subsequently, the vitality and growth of the lymphoblasts is determined with the aid of the vital dye 3-(4,5-dimethyl-2-thiazolyl)-2,5-diphenyltetrazolium bromide (MTT). For this 10 µl of an MTT solution (5 mg/ml in PBS) is added per microculture preparation and incubated at 37° C. for 4 hours. The blue formazan is dissolved by addition of 100 µl per microculture of a 10% SDS solution in 0.01 N HCl at 37° C. overnight. Afterwards the absorbance of the reacted dye is measured in an ELISA reader at a wavelength of 550 nm against a reference wavelength of 690 nm and the inhibition of the dye reaction in comparison to a control without monoclonal antibody against the IL-2 receptor is determined.

3. Result

Surprisingly, when a suitable combination of the two antibodies is used, one requires about a 15-fold lower antibody concentration than when in each case only one of the two antibodies is used alone (Table 1).

TABLE 1

The amount of monoclonal antibody against the IL-2 receptor required for a 60 to 70% inhibition of the IL-2-induced proliferation of pre-activated human peripheral blood lymphocytes in vitro is:

| Anti-α MAB 3G10/179 | Anti-β MAB C68/41 or A23A41 | Total conc. MAB | Reduction |
|---|---|---|---|
| 62.5 µg/ml | 0 µg/ml | 62.5 µg/ml | 0 |
| 12 µg/ml | 0.5 µg/ml | 12.5 µg/ml | 5-fold |
| 2 µg/ml | 2 µg/ml | 4 µg/ml | 15-fold |
| 0.5 µg/ml | 12 µg/ml | 12.5 µg/ml | 5-fold |
| 0 µg/ml | 62.5 µg/ml | 62.5 µg/ml | 0 |

What is claimed is:

1. An antibody composition comprising, (a) a monoclonal antibody, a chimeric monoclonal antibody containing human constant domains and murine variable domains, or a humanized monoclonal antibody, each of which specifically binds to high affinity IL-2R α chain and inhibits binding of IL-2 thereto and (b) a monoclonal antibody which specifically binds to high affinity IL-2R β chain and inhibits binding of IL-2 thereto, wherein said monoclonal antibody which specifically binds to said high affinity IL-2R β chain is C68/41 (ECACC 90090704) or A23A41 (DSM ACC2015), or is a chimeric monoclonal antibody which contains human constant domains and the variable domains of either C68/41 or A23A41, or is a humanized C68/41 or A23A41 monoclonal antibody.

2. An antibody composition of claim 1, said composition containing a total amount of antibodies comprising 1) 1–99% weight/volume monoclonal antibody which binds to high affinity IL-2R α chain and inhibits binding of IL-2 thereto and 2) 1–99% weight/volume monoclonal antibody which binds to high affinity IL-2R β chain and inhibits binding of IL-2 thereto, wherein said monoclonal antibody which binds to high affinity IL-2R α chain is present at 1 to 99% weight/volume of total amount of antibody, and wherein said monoclonal antibody which binds to high affinity IL-2R β chain is present at 1 to 99% weight/volume of total amount antibody.

3. An antibody composition of claim 1, said composition containing a total amount of antibodies comprising 1) 4 to 96% weight/volume monoclonal antibody which binds to high affinity IL-2R α chain and inhibits binding of IL-2 thereto and 2) 4 to 96% weight/volume monoclonal antibody which binds to high affinity IL-2R β chain and inhibits binding of IL-2 thereto, wherein said monoclonal antibody which binds to high affinity IL-2R α chain is present at 4 to 96% weight/volume of total amount of antibody, and wherein said monoclonal antibody which binds to high affinity IL-2R β chain is present at 4 to 96% of total amount antibody.

4. An antibody composition of claim 1, wherein said composition consists of equal amounts of each of said monoclonal antibody which binds high affinity IL-2R α chain and inhibits binding of IL-2 thereto and said monoclonal antibody which binds to high affinity IL-2R β chain and inhibits binding of IL-2 thereto.

5. An antibody composition of claim 1, wherein said monoclonal antibody which specifically binds to high affinity IL-2R α chain and inhibits binding of IL-2 thereto, comprises 3G10/179 (ECACC 90071905).

6. An antibody composition of claim 1, wherein said monoclonal antibody which specifically binds to high affinity IL-2R α chain and inhibits binding of IL-2 thereto is covalently coupled to said monoclonal antibody which specifically binds to high affinity IL-2R β chain and inhibits binding of IL-2 thereto.

7. An antibody composition of claim 1, wherein at least one of said monoclonal antibodies is the chimeric monoclonal antibody of (a) or (b).

8. An antibody composition of claim 1, wherein at least one of said monoclonal antibodies is the humanized monoclonal antibody of (a) or (b).

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
        (A) LENGTH: 322 base pairs
        (B) TYPE: nucleic acid
        (C) STRANDEDNESS: single
        (D) TOPOLOGY: linear (xi) SEQUENCE DESCRIPTION: SEQ ID NO: 1:

```
GAC GTC TTG CTG ACT CAG TCT CCA GCC ATC CTG TCC GTG AGT CCA GGA        48
Asp Val Leu Leu Thr Gln Ser Pro Ala Ile Leu Ser Val Ser Pro Gly
1               5                   10                  15

GAA AGA GTC AGT TTC TCC TGT AGG GCC AGT CAG AGC ATT GGC ACA AGC        96
Glu Arg Val Ser Phe Ser Cys Arg Ala Ser Gln Ser Ile Gly Thr Ser
            20                  25                  30

ATA CAC TGG TAT CAG CAA AGA ACA AAT GGT CCT CCA AGG CTT CTC ATA       144
Ile His Trp Tyr Gln Gln Arg Thr Asn Gly Pro Pro Arg Leu Leu Ile
35                  40                  45

AAG TAT GCG TCT GAG TCA ATC TCT GGG ATC CCT TCC AGG TTT AGT GGC       192
Lys Tyr Ala Ser Glu Ser Ile Ser Gly Ile Pro Ser Arg Phe Ser Gly
50                  55                  60

AGT GGA TCA GGG ACA GAT TTT ACT CTT AGC ATC AGC AGT GTG GAG TCT       240
Ser Gly Ser Gly Thr Asp Phe Thr Leu Ser Ile Ser Ser Val Glu Ser
65                  70                  75                  80

GAA GAT ATT GCA GAT TAT TAC TGT CAA CAA ACT AAT AGC TGG CCA ACC       288
Glu Asp Ile Ala Asp Tyr Tyr Cys Gln Gln Thr Asn Ser Trp Pro Thr
85                  90                  95

ACG TTC GGA GGG GGG ACC AAG CTG GAA ATT AAA C                         322
Thr Phe Gly Gly Gly Thr Lys Leu Glu Ile Lys
100                 105
```

(2) INFORMATION FOR SEQ ID NO:2:

(i) SEQUENCE CHARACTERISTICS:
        (A) LENGTH: 355 base pairs
        (B) TYPE: nucleic acid
        (C) STRANDEDNESS: single
        (D) TOPOLOGY: linear (xi) SEQUENCE DESCRIPTION: SEQ ID NO: 2:

```
GAG GTC CAG CTG CAA CAG TTT GGA GCT GAA TTG GTG AAG CCT GGG ACT        48
Glu Val Gln Leu Gln Gln Phe Gly Ala Glu Leu Val Lys Pro Gly Thr
1               5                   10                  15

TCG GTG AAG ATA TCC TGC AAG GCT TCT GGC TAC ATT TTC ACT GAC TAC        96
Ser Val Lys Ile Ser Cys Lys Ala Ser Gly Tyr Ile Phe Thr Asp Tyr
            20                  25                  30

AAC ATG GAC TGG GTG AAG CAG AGC CAT GGA AAG AGC CTT GAG TGG ATT       144
Asn Met Asp Trp Val Lys Gln Ser His Gly Lys Ser Leu Glu Trp Ile
35                  40                  45

GGA GAT ATT GAT CCT AAC TTT GAT AGT TCC AGT TAC AAC CAG AAG TTC       192
Gly Asp Ile Asp Pro Asn Phe Asp Ser Ser Ser Tyr Asn Gln Lys Phe
50                  55                  60

AAG GGA AAG GCC ACA TTG ACT GTA GAC AAG TCC TCC AAC ACA GCC TAC       240
Lys Gly Lys Ala Thr Leu Thr Val Asp Lys Ser Ser Asn Thr Ala Tyr
65                  70                  75                  80

ATG GAG CTC CGC AGC CTG ACA TCT GAG GAC ACT GCA GTC TAT TAC TGT       288
Met Glu Leu Arg Ser Leu Thr Ser Glu Asp Thr Ala Val Tyr Tyr Cys
85                  90                  95
```

```
-continued

GCA AGA GGG GGA TTC CCC TAT GGT ATG GAC TAC TGG GGT CAA GGA ACC      336
Ala Arg Gly Gly Phe Pro Tyr Gly Met Asp Tyr Trp Gly Gln Gly Thr
100             105                 110

TCA GTC ACC GTC TCC TCA G                                            355
Ser Val Thr Val Ser Ser
115
```